United States Patent [19]
Johnson

[11] Patent Number: 5,138,891
[45] Date of Patent: Aug. 18, 1992

[54] GAUGE WELL SYSTEM

[76] Inventor: Ronald G. Johnson, 14643 Plumosa Dr., Jacksonville, Fla. 32250

[21] Appl. No.: 481,961

[22] Filed: Feb. 20, 1990

[51] Int. Cl.⁵ .................. G01N 1/12; G01F 23/30
[52] U.S. Cl. .................. 73/864.67; 73/864.63; 73/306; 73/319; 374/157
[58] Field of Search ........... 73/863.81, 863.82, 863.83, 73/863.84, 863.85, 863.86, 864.63, 864.64, 864.65, 864.66, 864.67, 305, 306, 319, 322.5; 33/717–720, 722, 726, 727; 374/156, 157

[56] References Cited

U.S. PATENT DOCUMENTS

| | | | |
|---|---|---|---|
| 1,257,693 | 2/1918 | Furman | 73/306 X |
| 1,880,868 | 10/1932 | de Lancey | 73/864.63 |
| 2,004,568 | 6/1935 | Carpinello | 73/864.64 X |
| 2,650,499 | 9/1953 | Quist | 73/864.66 |
| 2,957,347 | 10/1960 | Bergstrom | 73/321 |
| 3,055,764 | 9/1962 | Pryor et al. | 73/864.63 |
| 3,129,513 | 4/1964 | Porter | 73/864.65 X |
| 3,380,168 | 4/1968 | Holden et al. | 73/864.63 X |
| 3,935,741 | 2/1976 | Zinsmeyer et al. | 73/313 |
| 4,451,986 | 6/1984 | Jones, Jr. | 33/720 |
| 4,468,975 | 9/1984 | Seyles et al. | 73/863.81 |

FOREIGN PATENT DOCUMENTS

| | | | |
|---|---|---|---|
| 2454089 | 12/1980 | France | 374/157 |
| 649857 | 2/1951 | United Kingdom | 374/157 |
| 872821 | 7/1961 | United Kingdom | 73/864.63 |
| 1377755 | 12/1974 | United Kingdom | 73/864.63 |

*Primary Examiner*—Tom Noland
*Attorney, Agent, or Firm*—Arthur G. Yeager

[57] ABSTRACT

A system for a gauge well in a liquid storage tank with a floating roof including a floatable container located inside the gauge well and having a flexible laterally or radially serrated flange extending outward from the float and in contact with the inside of the well pipe to prevent vapor from the liquid stock from rising in the pipe. There may be a pair of such flexible flanges vertically spaced apart with the lower seal being just above the level of the liquid stock in the well pipe. A tape is attached at its lower end to a weight in the well pipe below the float and its upper end is connected to a winch outwardly of the upper end of the well pipe. A vertical passageway through the float is provided for the tape to pass freely therethrough and the float is freely slidable on the tape. The container includes a closed opening which is selectively opened to fill with the liquid stock at any selected level in the tank. The container also supports a thermometer and a D-ring member on top of the container to extract the float from the fill pipe when the tape is inadvertently broken.

26 Claims, 5 Drawing Sheets

GAUGE WELL SYSTEM

BACKGROUND OF THE INVENTION

Liquid storage tanks, e.g., gasoline storage tanks, are commonly employed to store gasoline in open tanks having floating roofs resting on the liquid level, moving up and down as the liquid level changes. In order to measure the amount of liquid in each tank and to access its quality gauge wells have been used. Each gauge well is a pipe extending from above the floating roof to adjacent the bottom of the tank. A float is positioned inside the gauge well pipe to move up and down with the level of liquid stock, and periodically to take a sample of the stock for analysis. One of the problems with floats in the prior art has been that petroleum vapors escaped out the top of the gauge well pipe causing complaints about the pollution of the atmosphere. Furthermore, when samples were taken it was necessary to remove the float and replace it with a sample container. It was also found that taking samples was not reliable because the stock in the confined space in the gauge well would not be representative of the stock generally in the tank. Accordingly, the gauge well pipe was pierced by slots spaced up and down the length of the gauge well pipe. Burrs left from cutting the slots frequently fouled the float and hung the float on a burr thereby preventing it from its purpose and sometimes the cable or tape broke, allowing the sampler container to fall to the bottom of the pipe with no chance of ready retrieval. Typical of patents relating to such a system is U.S. Pat. No. 4,468,975 to Sayles. Also, the float of Sayles apparently was chosen such that the outside diameter of the float approximated closely the inside diameter of the gauge well pipe which caused problems of using same in a retrofitted pipe system.

It is an object of this invention to provide an improved system wherein the float and sample container are the same article. A further object is to provide a float which accomplishes the sealing function with little chance of becoming lodged on a burr or the like in the well pipe. It is another object of this invention to provide an improved system whereby a sample container may be retrieved if accidentally dropped in the gauge well pipe. Still other objects will become apparent from the more detailed description which follows.

BRIEF SUMMARY OF THE INVENTION

This invention relates to a gauge well system for sealing the slotted gauge well pipe closely above the liquid stock in a storage tank having a floating roof with such gauge well pipe extending from the bottom of the tank upward through the roof to adjacent the upper extremities of the tank. A hollow cylindrical float adapted to move upward and downward through the well pipe includes a flexible vapor barrier flange connected to and extending laterally outward from the float and having a free edge portion in contact within and to the well pipe and adapted to prevent vapor from the liquid stock to pass by and to maintain the float generally centered in the well pipe. A cylindrical weight in the well pipe is disposed adjacent the bottom of the tank and attached thereto is an elongated tape extending upwardly through the float and adapted to be connected to a winch adjacent the top of the well pipe for raising and lowering the weight and the float. A tape guide includes a protective pipe around the tape inside and centrally of the float along its longitudinal axis.

In preferred embodiments the barrier flange includes a plurality of spaced and substantially radial slits from the free edge portion terminating short of the float to provide a plurality of flaps which enhance the sealing of the gauge well pipe with respect to its slots and internal burrs. To further seal off the vapors a flexible disc having a slit therein for slidably receiving the tape therethrough for sealing the passageway through the pipe and the tape as the float moves along the tape on the upper level of the liquid stock in the storage tank. Preferably, another flexible vapor barrier flange is connected to and extends laterally outward from the float and having a free edge portion in contact within and to the well pipe. The first mentioned barrier flange is located adjacent the top of the float and the other barrier flange is spaced downwardly from the barrier flange and substantially parallel thereto and closely adjacent the upper level of the liquid stock in the storage tank.

Some aspects of the invention are directed to the measuring of the liquid stock in the storage tank wherein the weight is selectively attachable to and located below the float or container and inside the well pipe with a linear measuring means on the tape and the container and the weight for measuring the liquid stock in the storage tank; and winch means outwardly of the top of the well pipe connected to the tape for raising and lowering the container and weight in the well pipe.

Additional aspects relate to the taking of a sample of liquid stock in the storage tank wherein an openable and closeable passageway is located through the cover of the float or container and communicates with the hollow of the container. A selective means is removably positioned in the passageway for opening and closing same. The selective means includes a stopper removable from the passageway, lever means attached at one end to the stopper for forcibly removing the stopper from the passageway to open the passageway for flow of fluid therethrough, and a weight slidably attached to the tape and for selectively applying a force on the lever means for removal of the stopper, the weight being dropped by an operator above the floating roof of the storage tank. A vent pipe communicates from inside the container adjacent the bottom thereof to outside of the cover, and a selectively removable cap is engaged with the vent pipe outwardly of the cover. The weight includes a plurality of depending legs and the depth measuring means includes a linear measurement gauge extending from a free end of one of the legs to the upper end of the container defined by the top cover of the container and continuing on the tape thereabove. The container includes a means for carrying a thermometer to determine the temperature of the liquid stock in the tank. The container also includes a well for the thermometer in which a portion of the liquid stock is captured to maintain the correct temperature of the liquid stock until removal of the container from the top of the well pipe. The cover additionally includes an eye means adjacent the tape guide or pipe and adapted to be caught by a hook at the end of a line dropped through the gauge well pipe to recover the float or container if the tape becomes detached from the weight. The system also includes a detachable connection means between the closed bottom of the container and the weight which includes a plurality of spaced bolt heads extending downwardly on either the bottom or the weight and interfitting into key type of T-slots in the other.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 2:
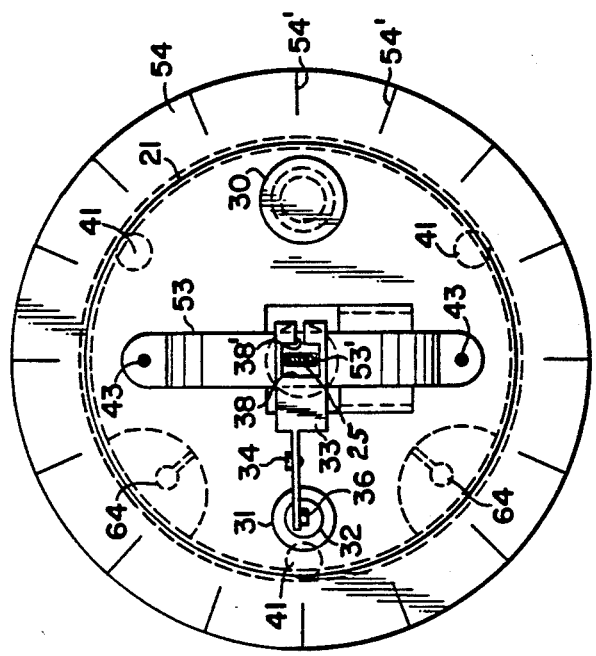
FIG. 2 is a top plan view of the container of FIG. 1.
Figure 1:
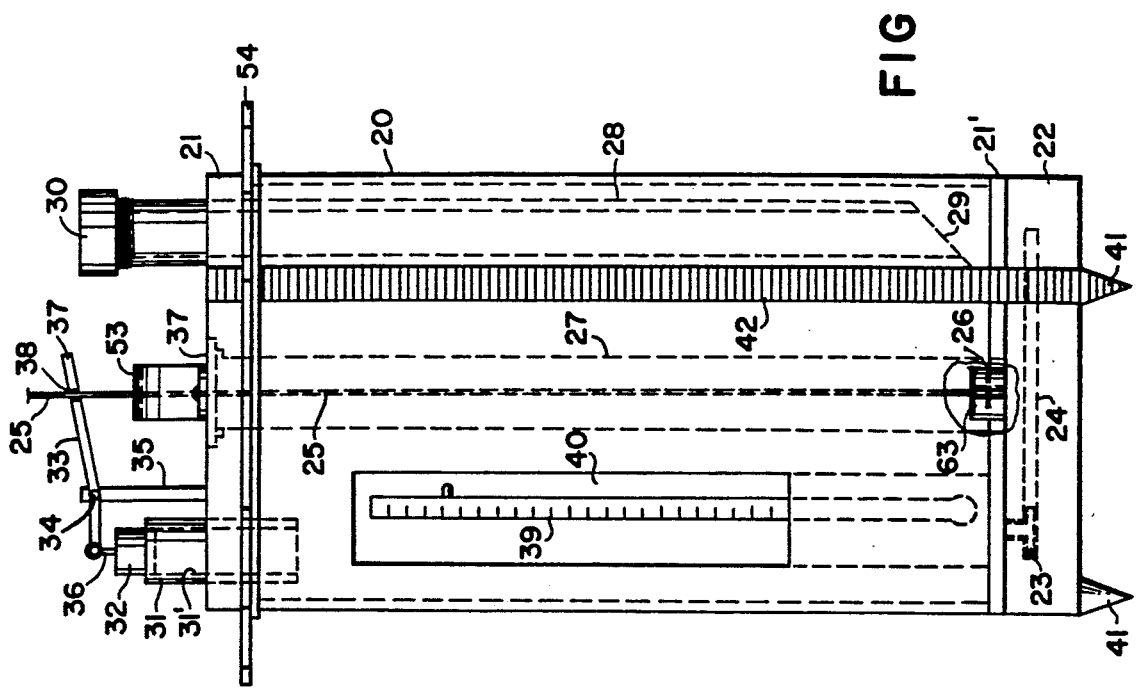
FIG. 1 is a front elevational view of the selectively floatable and sinkable container of this invention.

The invention is best understood by reference to the attached drawings. In FIGS. 1-2 there is seen the floatable container comprising a hollow body 20, a top cover 21, a bottom cover 21' and a bottom weight 22. Cover 21 is attached to body 20 by means of a plurality of screws 41. A tape 25 extends from the top of the gauge well pipe to weight 22 which normally will be detached from container body 20 and be hanging near the bottom of the storage tank.

Figure 4:
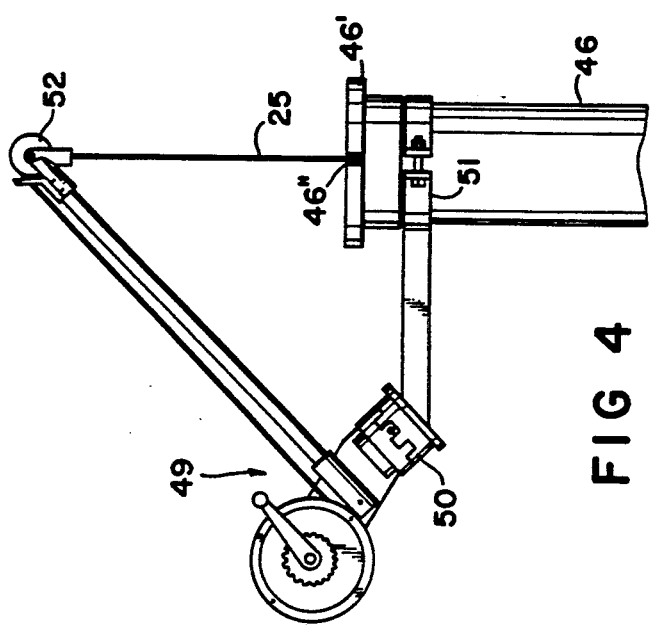
FIG. 4 is a side elevational view of the winch employed by this invention.
Figure 3:
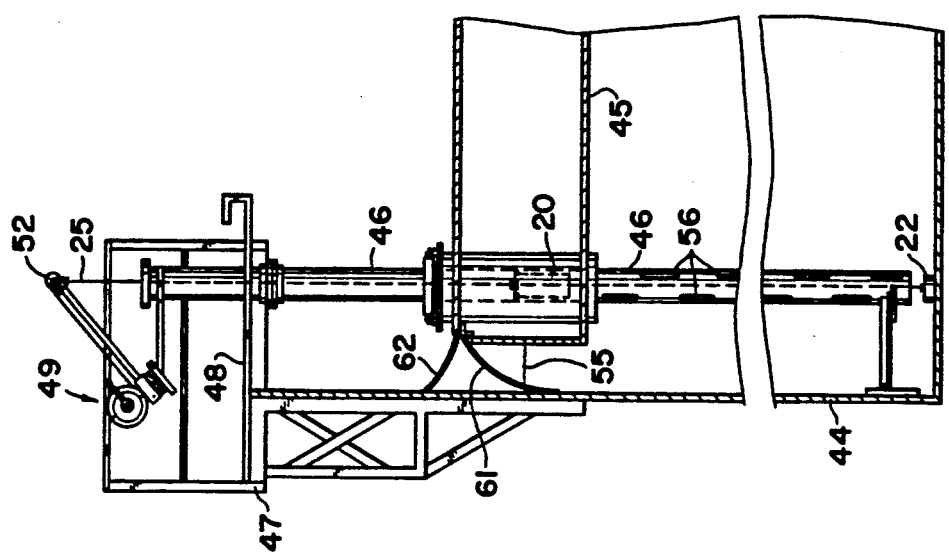
FIG. 3 is a side elevational view of a storage tank with the gauge well system of this invention.

The general features of the storage tank and the relation of this invention thereto is seen in FIGS. 3-4. Storage tank 44 is filled with a liquid stock to a level 55, and covered by a floating roof 45 which traps air between liquid stock level 55 and the structure of roof 45 to make it float. Around the edges of roof 45 there are two flexible rubber seals, i.e., primary seal 61 and secondary seal 62 which keep vapors from escaping to the atmosphere and also keep rain water from getting into storage tank 44. Some rain water normally does get into the stock and will, of course, form a layer at the bottom of storage tank 44 which occasionally is drained out.

Gauge well pipe 46 is fixed rigidly to the inside of tank 44 and extends through floating roof 45 which moves up and down around fixed pipe 46 as the level 55 of stock in tank 44 changes. Pipe 46 is perforated with a plurality of slotted openings 56 usually about one inch wide and about twelve inches long through the pipe wall to permit full mixing of the stock in the pipe with the stock outside of the pipe. An inspection structure 47 is built onto tank 44 with a platform 48 which extends toward the center of floating roof 45 to facilitate inspection of the tank 44 and its roof 45. Gauge well pipe 46 is placed so as to be conveniently available to a worker on platform 48. The upper end of pipe 46 may have a closure cap to be used when pipe 46 is not being used for the taking of samples, the measurement of stock levels, or the like. When used for such, however, there is a winch means 49 strapped to pipe 46 at 51 with a universal joint 50 to adjust the arm of winch 49 to an appropriate position to place pulley 52 over the open top end of pipe 46 so as to permit tape 25 to hang down the general center axis of pipe 46 even when the cover 46' is closed via lateral slot 46'' extending from an edge to medially of cover 46'. Winch means 49 is employed to crank up tape 25 and anything attached thereto when desired. At the other end of tape 25 is disc weight 22, preferably having a centering tongue or boss 63 which slides into a corresponding recess in the bottom of container body 20, including bottom cover 21'. Tape 25 is suitably connected to boss 63 by an attachment means 26 which includes a tapered pin force fit and extending through boss 63 and tape 25, tape 25 having been positioned via a slot cut into the side of boss 63. Normally weight 22 will be located near the bottom of well pipe 46 close to or on the bottom of tank 44 when the container body 20 is used as a float and seal. Tape 25 extends upwardly through a vertical pipe sheath 27 or the like extending vertically through and attached to the container body 20 and through cover 21 to winch means 49.

Figure 9:
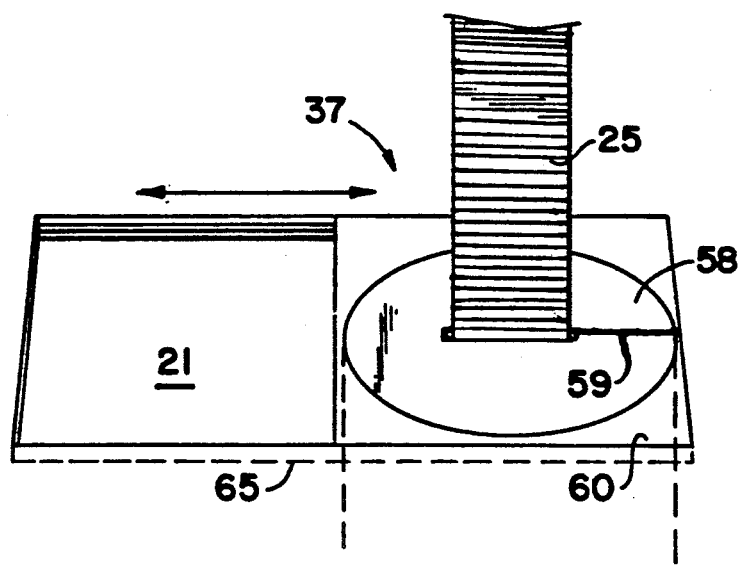
FIG. 9 is a perspective view of a portion of the upper container cover showing details of the sealing means of the suspension tape.

When container body 20 and covers 21 and 22 are functioning as a float it is not affected by tape 25 but merely slides up and down tape 25 as the level 55 of stock in tank 44 may change. The pipe sheath 27 extends through the central vertical axis of container body 20 surrounding tape 25. Top cover 21 has a sealing means 37 with a slotted passageway to permit tape 25 to freely pass into and out of container body 20. As may be seen in FIG. 9 the sealing means 37 includes a rubber seal 58 set in a plate 60 on top cover 21 where tape 25 passes through. A slit 59 in rubber seal 58 keeps tape 25 sealed to prevent vapor passage upwardly through passageway 27. Also, this seal 58 may be slid laterally in the same direction as slot 59 along guides 65 attached to cover 21 so as not to interfere or wipe off gauge paste which may be applied to the tape for determining liquid levels in tank 44. It may be seen that when in the float mode container 20 will slide over tape 25 freely and the seal 58 does not interfere with such float mode.

Figure 8:
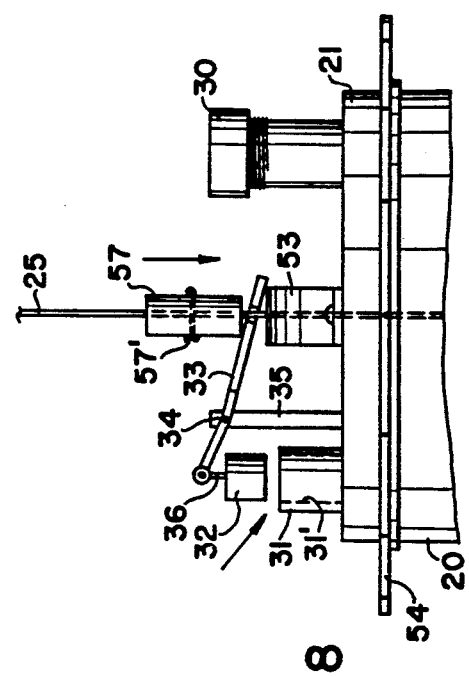
FIG. 8 is a front elevational view of the upper cover of the container of this invention illustrating the operation of the stopper removal system to take a sample.

When container body 20 is to be used as a sample collector there are other features that are important. A short pipe nipple 34 or the like forms an open passageway 31' which extends through for stock to enter or be poured out of container body 20. Stopper 32 normally closes the passageway 31'. In order to be able to take the sample at any selected depth in the liquid stock there is a lever mechanism designed to selectively remove stopper 32 when desired. A lever 33 has a fulcrum at 34 supported by a suitable structure 35 mounted to the outside of cover 21. At one end of lever 33 there is a connecting link 36 to stopper 32. At the other end of lever 33 there is a slot 38 to permit tape 25 to pass through and another intersecting slot 38' to permit insertion of the tape 25 into slot 38. When the selected depth is reached, as indicated on the tape 25 or on an indicator associated with winch means 49 (not shown) for taking a sample, a slotted weight 57 (see FIG. 8) with cotter pin 57' slidingly connects the weight to the tape 25 and such weight 57 is slid down tape 25 from above to fall upon the end of lever 33 at tape 25. The force of the falling weight 57 acts through the lever 33 to retract stopper 32 from pipe nipple 31 as shown in FIG. 8. Thus stock will flow through the open passageway 31' into container 20 and permits a sample from the stock to be taken at the depth selected. It is of little consequence that stopper 32 is not returned to close passageway 31' after the sample is taken. The upward movement of sample body 20 and cover 21 after taking the sample will not cause any material changes in the contents of the sample in container 20.

Container body 20 also has two wells 64 for thermometers 39 to record the temperature of the sample. Container body 20 has a sight window 40 at each well to facilitate reading the temperature. Wells 64 at the bottom of the thermometers provide maintenance of the temperature of the thermometers during withdrawal of the body 20 from the gauge well 46 for more accurate reading by the operator above the tank 44.

A selectively openable vent tube 28 is also provided in container body 20 comprising a tube with an open bottom end 29 and a screw top closed with a cap 30. Vent tube 28 is principally useful when emptying container body 20 of a sample of stock. Cap 30 may be removed to provide air to break any vacuum that might otherwise develop in pouring the sample out of passageway 31.

The weight 22 includes at least three legs 41 extending from below the lower surface of disc weight 22. Preferably these legs 41 are pointed so as to pierce any sludge at the bottom of the storage tank 44 when the weight 22 with or without container 20 is dropped that far, which might be the case in determining whether there is water and/or sludge at the bottom of storage tank and for gauging the tank. A measuring tape 42 or the equivalent is placed on the side of container body 20 to measure the depth of water or sludge. It is well known that a paste is applied to measuring tapes today which paste reacts to water, but not to petroleum, and in this fashion the depth of water may be determined. Likewise, another paste applied to the tape at about the approximate level (determined from outside level indicator, not shown) of the petroleum level 55 is wiped onto the tape which reacts to petroleum and thereby gauges the level 55.

Figure 7:
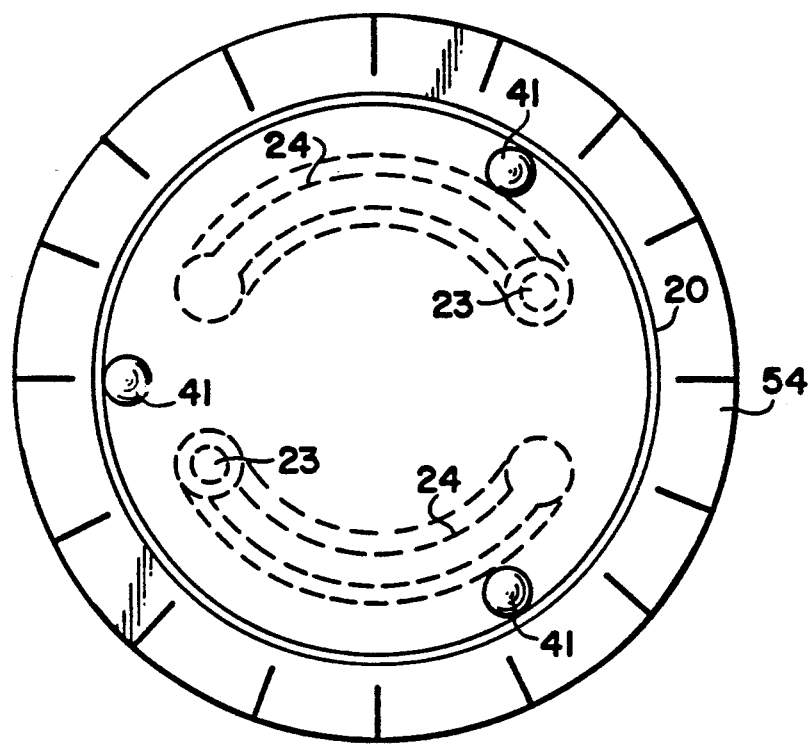
FIG. 7 is a bottom plan view of the container of FIG. 6.

Disc weight 22 is shown as having keyway slots 24 therein to fit bolt heads 23 in the bottom of container body 20 (see especially FIG. 7). If it is desired to make container body 20 sink, then disc weight 22 is attached to overcome the buoyancy of the float body 20. Such would be the case in taking samples of the stock or gauging the petroleum level or water level.

Another useful feature of this invention is a D-ring or handle 53 attached by screws 43 to cover 21 adjacent to tape 25. Preferably D-ring or handle 53 has a slot 53' therethrough for tape 25 to freely pass, and a lateral slot 53" similar to lateral slot 38'. It is only necessary to have D-ring or handle 53 very close to tape 25 or the handle 53 may be formed to two spaced D-portions on opposite sides of tape 25. The purpose of D-ring or handle 53 is to provide a catch for retrieving container body 20 in the event tape 25 should break and container body 20 should fall to the bottom of well pipe 46. A weighted line with a grappling hook could then be suspended down well pipe 46 and manipulated to cause the hook to catch D-ring or handle 53 which could then retrieve container body 20.

Well pipe 46 has spaced slotted perforations 56 to permit good mixing of stock inside and outside of well pipe 46. These perforations, however, sometimes have burred edges inside pipe 46 which may damage or entangle a float of the type shown in the aforesaid Sayles patent. It is therefore, important to have a flexible seal 54 and a smaller diameter body 20 to permit unobstructed flotation and or sinking of body 20 via the weight attachment 22. A D-ring or handle 53 is available to retrieve container body 20 when the tape 25 is broken.

Figure 5:
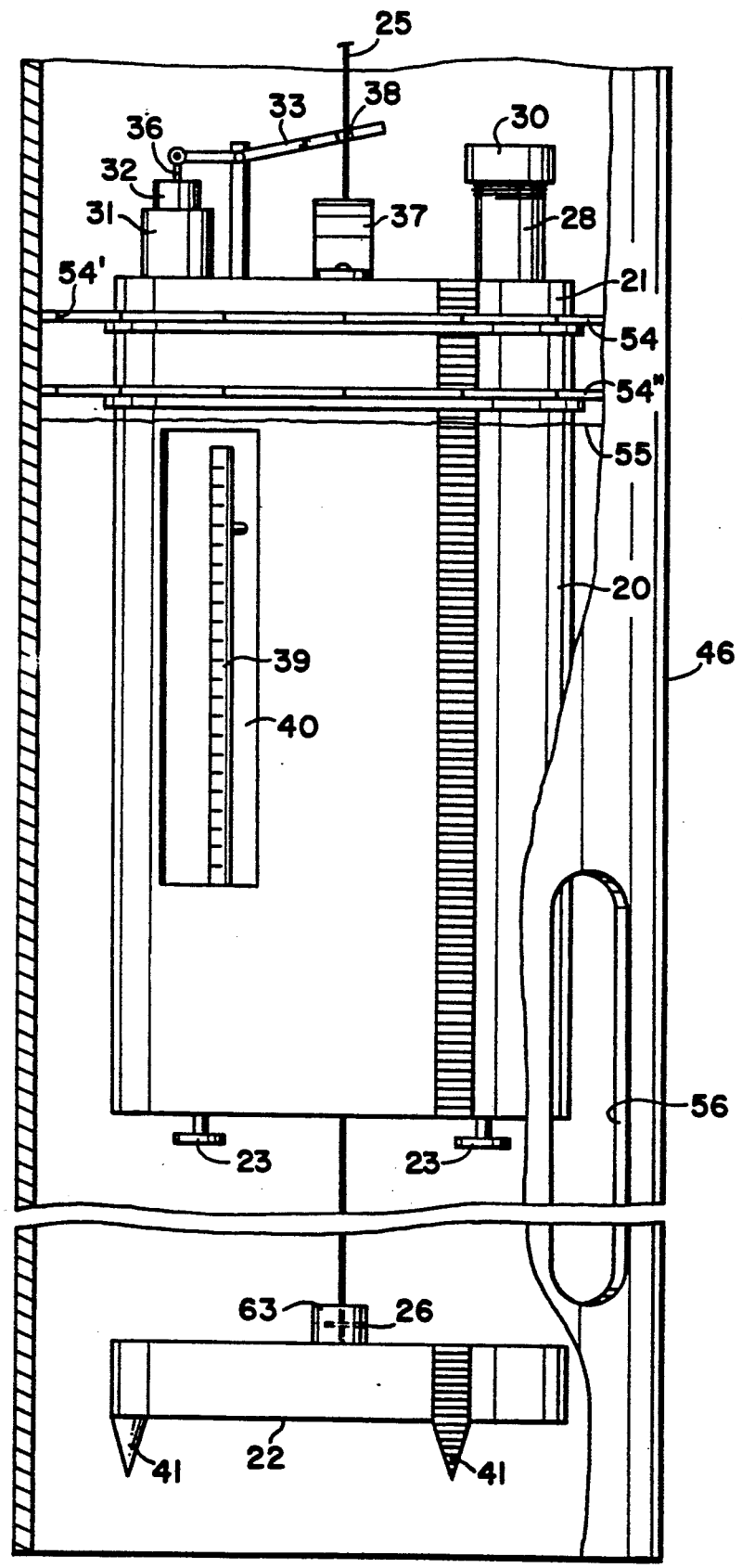
FIG. 5 is a front elevational view similar to that of FIG. 1 showing the container floating in the gauge well pipe.
Figure 6:
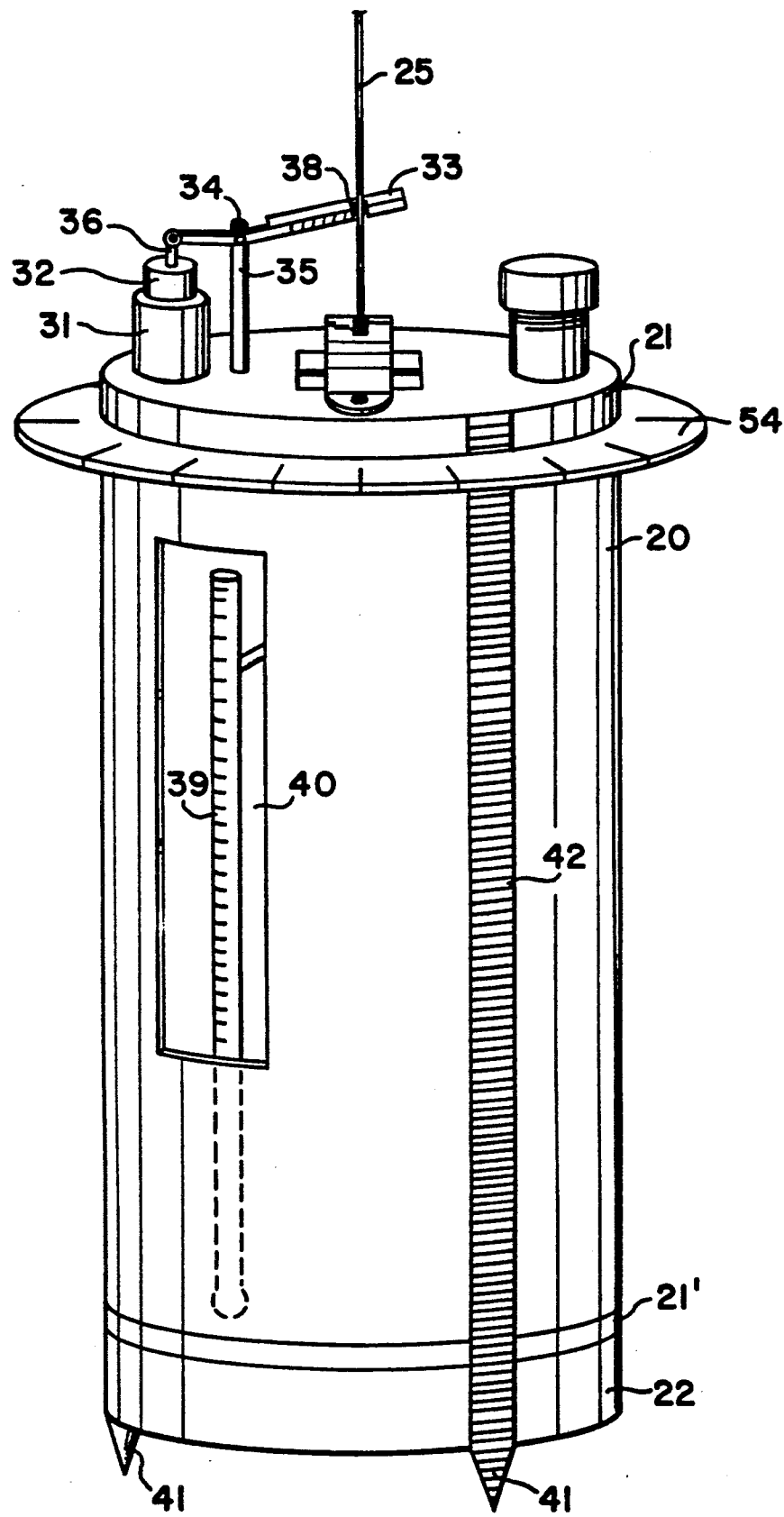
FIG. 6 is a perspective view of the container with the bottom weight attached thereto.

The opposed perforations 56 are 180° apart and are offset 90° so that the top of the perforation on one side of the pipe 46 will be at the bottom of the perforation on the side 90° therefrom. As seen in FIGS. 2 and 5 the seal 54 is preferably of Buna N and is connected between cover 21 and the upper end of container body 20. Seal 54 is seen to include a plurality of radial slits 54' having a length of about three-fourths of an inch and which terminate short of body 20. Preferably the slits are about three-fourths of an inch apart so that they will not become hung on the slots 56 or the burrs. Also, another seal 54" should be mounted on the container body 20 such that the seal is just above the liquid level 55 to maximize the effectiveness of the sealing of the gauge well pipe 46 by the container 20 hereof.

Of course, when it is desired to remove the container 20 from the well pipe 46, the winch means 49 is cranked up and the weight 22 engages the bottom cover 21' and moves same upwardly and out the open upper end of well pipe 46, i.e., cover 46' is pivoted or removed, as the case may be, to completely open the upper end of pipe 46.

The Sayles patented device even when working freely restricts or recovers between 60% and 70% of the aromatics normally lost through the well pipe whereas the instant invention recovers 90% to 98% of same. When a float like that shown by the Sayles patent was used, the float often lodged onto a burr because the outside diameter of such float was chosen to be very close to the inside diameter of the gauge well pipe. The instant container 20 is intentionally made some two inches less in diameter to the inside diameter of the gauge well pipe 46 to insure that it does not become lodged by a burr. The Buna-N rubber seal 54 and/or 54" conforms in shape around the burr and slots in the well pipe to maximize the effectiveness of the seal against vapor escaping through the well pipe 46. Employment of a winch and a tape improves the various attributes of the system and reduces the amount of contact by the worker with the petroleum or other chemicals in the tank 44, i.e., the cable of the Sayles patent must be pulled up by hand, for example, after detachment from the cover, or the like.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. In a gauge well system for measuring and taking a sample of liquid stock in a storage tank having a floating roof, a slotted gauge well pipe extending through the roof; the improvement which comprises
    (a) a hollow cylindrical floatable container having a closed bottom and a top cover;
    (b) a flexible sealing flap extending outwardly from said container and adapted to contact the inside of the well pipe without lodging of the flap on any burrs in the well pipe;

(c) an openable and closeable passageway through said cover communicating with the hollow of said container;

(d) selective means for opening and closing said passageway;

(e) a generally cylindrical weight located below said closed bottom of said container and inside the well pipe, said weight having a diameter substantially equal to the diameter of said cylindrical container;

(f) a windable tape attached to said weight and extending upwardly through a vertical passageway in said bottom, an aligned passageway through said container and through another aligned passageway in said cover and upwardly to the upper end of the well pipe;

(g) and winch means located outwardly of the top of the well pipe connected to said tape for raising and lowering said container and said weight in said well pipe.

2. The system of claim 1 which additionally includes an upstanding member attached to and above said cover permitting ready extraction of said container upon breakage of said tape.

3. The system of claim 2 which includes an elastomeric disc carried by said cover with a slit therein through which said tape passes.

4. The system of claim 1 wherein said selective means includes a stopper removable from said passageway, lever means attached at one end to said stopper for forcibly removing said stopper from said passageway to open said passageway for flow of fluid therethrough, and another weight slidably attached to said tape and for selectively applying a force on said lever means for removal of said stopper, said another weight being dropped by an operator above the floating roof of the storage tank.

5. The system of claim 1 which additionally comprises a vent pipe communicating from inside said container adjacent the bottom thereof to outside of said cover, and a selectively removable cap on said vent pipe.

6. The system of claim 1 wherein said container additionally includes a plurality of spaced legs on said weight and extending therebelow, a depth measuring means extending along and carried by said container to determine the depth of sludge or a nonmiscible liquid layer at the bottom of the storage tank.

7. The system of claim 6 wherein said depth measuring means includes a linear measurement gauge extending from a free end of one of said legs to the upper end of said container defined by said top cover.

8. The system of claim 1 wherein said container includes means for carrying a thermometer.

9. The system of claim 8 wherein said container includes a well for said thermometer in which a portion of the liquid stock is captured to maintain the correct temperature of the liquid stock until removal of the said container from the top of the well pipe.

10. The system of claim 1 wherein said container additionally includes an elongated tube disposed within said container and extending through said top cover, and a removable cap selectively sealing said tube above said top cover.

11. The system of claim 1 wherein said cover additionally includes an eye means adjacent said tape guide and adapted to be caught, a hook at the end of a line dropped through said gauge well pipe to recover said float if said tape becomes detached.

12. The system of claim 1 further comprising detachable connection means between said closed bottom of said container and said weight, said connection means including a plurality of spaced bolt heads extending downwardly on one of said bottom and said weight and interfitting into key type of T-slots in the other of said bottom and said weight.

13. The system of claim 1 wherein said sealing flap includes a plurality of spaced and generally radial slits to provide enhanced sealing within the slotted well pipe about the slots and burrs therein.

14. The system of claim 1 wherein said sealing flap includes a plurality of spaced and substantial radial slits from its free edge portion terminating short of said container to provide a plurality of tabs which enhance the sealing of the well pipe with respect to its slots and internal burrs.

15. In a gauge well system for measuring and taking a sample. of the liquid stock in a storage tank having a floating roof and a slotted gauge well pipe having an internal cylindrical passageway extending from a bottom of the tank upward through the roof to adjacent the upper extremities of the tank; the improvement comprising (a) a hollow cylindrical float adapted to move upward and downward through the passageway of the well pipe, said float having a removable upper cover, a flexible vapor barrier flange extending laterally outward from said float to the passageway of the well pipe and adapted to inhibit vapor from the liquid stock to upwardly escape and to maintain the float generally centered in the passageway of the well pipe;

(b) a weight detachably connected to said float;

(c) an elongated tape attached to said weight below and extending upwardly through said float for connection to a winch means adjacent an upper end of said well pipe and adapted to raise and lower said weight;

(d) a tape guide including a protective hollow pipe around said tape extending through said float, said cover having an opening therethrough aligned with the hollow of said pipe, a flexible disc across said opening and having a slit therein for the passage of said tape therethrough;

(e) a passageway through said cover and a selectively removable stopper therein for opening said passageway and the hollow of said float to the surrounding liquid stock for filling thereof; and (f) means for selectively removing said stopper at any selected depth of said float below the level of the liquid stock in the storage tank.

16. The system of claim 15 wherein said means for removing said stopper includes a fulcrum on said upper cover and an elongated lever disposed across said fulcrum having one end of said lever attached to said stopper and the other end of said lever being positioned adjacent said tape, and a weight adapted to be selectively and slidably positioned on said tape adjacent its upper end above the floating roof of the storage tank and slidable downwardly to engage said other end of said lever to withdraw said stopper from said passageway through said cover.

17. The system of claim 15 which additionally comprises a pipe passing generally vertically through said upper cover and extending from an open end at the inside bottom of said container to an upper end above said upper cover, and removable cover means for selectively closing said upper end of said pipe.

18. The system of claim 15 wherein said float includes a thermometer to measure the temperature of the liquid stock at any selected level in the storage tank.

19. The system of claim 15 wherein said float includes a plurality of pointed legs extending downwardly below its bottom, and linear measurement means extending from said upper cover to the bottom of one of said legs and continuing on said tape.

20. The system of claim 15 wherein said float includes a D-ring rigidly attached to said upper cover and extending upwardly therefrom and adapted to provide a catch for a hook which is lowerable to retrieve said float upon tape failure from the well pipe.

21. In a gauge well system for measuring liquid stock in a storage tank having a floating roof, a slotted gauge well pipe extending through the roof; the improvement which comprises
   (a) a hollow cylindrical floatable container having a closed bottom and a top cover;
   (b) a flexible sealing flap extending outwardly from said container and adapted to contact the inside of the well pipe;
   (c) a weight and elective means for attaching said weight to said container and located below said container and inside said well pipe;
   (d) a windable tape attached to said weight and extending upwardly through a passageway in said container through an aligned passageway in said cover and upwardly to the upper end of the well pipe;
   (e) linear measuring means on said tape and said container and said weight for measuring the liquid stock in the storage tank; and
   (f) winch means outwardly of the top of the well pipe connected to said tape for raising and lowering said container and weight in said well pipe.

22. In a gauge well system for sealing the slotted gauge well pipe closely above the liquid stock in a storage tank having a floating roof with such gauge well pipe extending from the bottom of the tank upward through the roof to adjacent the upper extremities of the tank; the improvement comprising
   (a) a hollow cylindrical float adapted to move upward and downward through the well pipe;
   (b) a flexible vapor barrier flange connected to and extending laterally outward from said float and having a free edge portion in contact within and to the well pipe and adapted to prevent vapor from the liquid stock to pass by and to maintain the float generally centered in the well pipe;
   (c) a cylindrical weight in the well pipe adjacent the bottom of the tank;
   (d) an elongated tape attached to said weight and extending upwardly through said float and adapted to be connected to a winch adjacent the top of the well pipe for raising and lowering said weight and said float; and
   (e) a tape guide including a protective pipe around said tape inside and centrally of said float along its longitudinal axis.

23. The system of claim 22 wherein said barrier flange includes a plurality of spaced and substantially radial slits from said free edge portion terminating short of said float to provide a plurality of flaps which enhance the sealing of the gauge well pipe with respect to its slots and internal burrs.

24. The system of claim 22 further comprising a flexible disc, a passageway through said cover aligned with said pipe, said disc having a slit therein for slidably receiving said tape therethrough for sealing said passageway around said tape as said float moves along said tape on an upper level of the liquid stock in the storage tank.

25. The system of claim 24 further comprising another flexible vapor barrier flange connected to and extending laterally outward from said float and having a free edge portion in contact within and to the well pipe, said barrier flange being located adjacent a top of said float, said other barrier flange being spaced downwardly from said barrier flange and substantially parallel thereto and closely adjacent the upper level of the liquid stock in the storage tank.

26. The system of claim 25 wherein said barrier flange and said other barrier flange each includes a plurality of spaced and substantially radial slits from said free edge portion terminating short of said float to provide a plurality of flaps which enhance the sealing of the gauge well pipe with respect to its slots and internal burrs.

* * * * *